United States Patent
Van Der Schaaf et al.

(10) Patent No.: US 6,465,554 B1
(45) Date of Patent: Oct. 15, 2002

(54) RUTHENIUM AND OSMIUM CARBENE CARBONYL CATALYSTS

(75) Inventors: Paul Adriaan Van Der Schaaf; Roman Kolly, both of Allschwil; Andreas Mühlebach, Frick; Andreas Hafner, Gelterkinden, all of (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/647,031

(22) PCT Filed: Mar. 22, 1999

(86) PCT No.: PCT/EP99/01914

§ 371 (c)(1),
(2), (4) Date: Sep. 25, 2000

(87) PCT Pub. No.: WO99/50330

PCT Pub. Date: Oct. 7, 1999

(30) Foreign Application Priority Data

Mar. 31, 1998 (CH) .............................................. 774/98

(51) Int. Cl.$^7$ ................................................. C08K 3/18
(52) U.S. Cl. ........................ 524/403; 502/435; 556/136; 526/171; 526/172; 522/66
(58) Field of Search .......................... 502/36; 556/136; 526/280, 308, 190, 171, 172, 222, 233, 93; 528/490, 491; 522/66, 114

(56) References Cited

U.S. PATENT DOCUMENTS

| | | | | |
|---|---|---|---|---|
| 5,312,904 A | * | 5/1994 | Grubbs et al. | 556/136 |
| 5,342,909 A | * | 8/1994 | Grubbs et al. | 526/171 |
| 5,606,085 A | * | 2/1997 | Bell et al. | 556/57 |
| 5,710,298 A | * | 1/1998 | Grubbs et al. | 556/22 |
| 5,728,785 A | * | 3/1998 | Grubbs et al. | 526/142 |
| 5,854,299 A | * | 12/1998 | Muhlebach | 522/66 |
| 5,922,802 A | * | 7/1999 | Setiabudi | 524/482 |
| 5,932,664 A | * | 8/1999 | Chen et al. | 525/338 |
| 6,147,026 A | * | 11/2000 | Setiabudi et al. | 502/162 |
| 6,171,995 B1 | * | 1/2001 | Muhlebach et al. | 502/162 |
| 6,225,488 B1 | * | 5/2001 | Mukerjee et al. | 556/22 |
| 6,284,852 B1 | * | 9/2001 | Lynn et al. | 526/171 |
| 6,291,616 B1 | * | 9/2001 | Kiessling et al. | 526/171 |

FOREIGN PATENT DOCUMENTS

| | | |
|---|---|---|
| EP | 0 771 830 | 5/1997 |
| WO | 93/20111 | 10/1993 |
| WO | 96/04289 | 2/1996 |
| WO | 97/20865 | 6/1997 |

OTHER PUBLICATIONS

Esteruelas, M.A.; Lahoz, F. J.; Onate, E.; Oro, L.A.; Zeier, B. Organometallics 1994, 13, 1662.*

Esteruelas, M.A.; Lahoz, F. J.; Onate, E.; Oro, L. A.; Zeier, B. Organometallics 1994, 13, 4258.*

Shriver, D.F.; Atkins, P.W.; Langford, C. H. Inorganic Chemistry W. H. Freeman and Company: New York, 1990, pp. 511–512.*

Esteruelas, M.A.; Wener, H. J. Organomet. Chem. 1986, 303, 221.*

Organometallics, vol. 13, No. 11, pp. 4258–4265 (1994), Not Received.

* cited by examiner

Primary Examiner—David W. Wu
Assistant Examiner—Rip A. Lee
(74) Attorney, Agent, or Firm—Kevin T. Mansfield; Tyler A. Stevenson

(57) ABSTRACT

The invention relates to compositions of hexacoordinated ruthenium and osmium carbenes with a carbonyl group as ligand and a vinyl group as substituent on the carbene group as catalysts for the photoinduced ring-opening metathesis of strained cycloolefins. It also relates to novel hexacoordinated ruthenium and osmium carbenes having a carbonyl group as ligand and a vinyl group as substituent on the carbene group, to compositions of the catalyst with cycloolefins, and to the polymerization process.

7 Claims, No Drawings

RUTHENIUM AND OSMIUM CARBENE CARBONYL CATALYSTS

The invention relates to compositions of hexacoordinated ruthenium and osmium carbene carbonyl catalysts and to their use for the photoinduced synthesis of polymers, to novel coordinated ruthenium and osmium carbene carbonyl catalysts, and to processes for their preparation.

The metathesis polymerization of cycloolefins (ROMP: Ring Opening Metathesis Polymerization) which are under ring strain, which has acquired great importance in recent times, requires appropriate catalysts. Catalysts of particular interest for the application are so-called metal carbenes, i.e. transition metal compounds—ruthenium and osmium compounds, for example—having a group=CR'R" attached to the metal atoms [WO 93/20111; S. Kanaoka et al., *Macromolecules* 28: 4707–4713 (1995); C. Fraser et al., *Polym. Prepr.* 36:237–238 (1995); P. Schwab et al., *Angew. Chem.* 107: 2179–2181 (1995)]. Suitable catalysts for photoinduced ROMP are described in WO 95/07310 and WO96/16103. Their applicability is limited by their cationic nature or low reactivity.

M. A. Esteruelas et al. in *Organometallics*, Vol. 13: 4258–4265 (1994) describe some hexacoordinated ruthenium and osmium carbenes of the formula

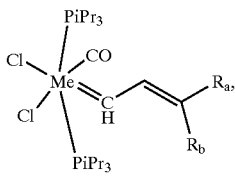

in which one of the radicals $R_a$ and $R_b$ is hydrogen and the other is phenyl or both are phenyl, but do not indicate the possibility of their use for ROMP.

It has surprisingly been found that hexacoordinated ruthenium and osmium carbenes having a carbonyl group as ligand and a vinyl group as substituent on the carbene group are excellent catalysts for photoinduced ring-opening metathesis. Through an appropriate choice of neutral ligands it is possible to exercise close control over the reactivity, for example the latency, over a wide range.

The invention provides compositions comprising (α) a cycloolefin or a mixture of cycloolefins; and (β) a catalytic amount of at least one compound

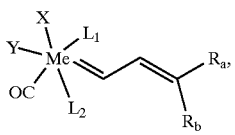

(I)

in which

Me is ruthenium or osmium;

X and Y independently of one another are anionic ligands or together are a bis-anionic ligand;

$L_1$ and $L_2$ independently of one another are neutral ligands having electron donor properties and $R_a$ and $R_b$ independently of one another are hydrogen or hydrocarbon radicals, and isomers of these compounds.

One particular embodiment provides compounds (I) in which Me is ruthenium, and also provides for their use.

Compounds (I) have the advantage that cyclic olefins, such as dicyclopentadiene (DCPD), can be polymerized in a photoinduced metathesis polymerization using a one-component catalyst. It has also been found that the polymerization takes place even in the presence of polymer additives, such as fillers, and that mouldings, films or coatings having excellent physical and mechanical properties are obtained. It has been observed, further, that the compositions comprising cyclic olefin and the compounds of the invention are stable to air and moisture and therefore exhibit great stability on storage. No particular protective measures are necessary for the polymerization, which offers considerable advantages in processing. It has also been found that, using these catalysts, DCPD can be copolymerized with other strained cycloolefin comonomers. This makes it possible to carry out controlled modification of properties and to adapt them to the desired end use.

The designations used in describing the present invention are defined as follows:

Suitable anionic ligands X and Y are, for example, the hydride ion (H⁻) or are ligands derived, for example, from organic or inorganic acids by elimination of protons, an example being halide (F⁻, Cl⁻, Br⁻ and I⁻) or anions of oxygen acids or derivatives thereof, e.g. $SnCl_6^{2-}$, $BF_4^-$, $PF_6^-$, $SbF_6^-$ or $AsF_6^-$.

Anions of oxygen acids are, for example, sulfate, phosphate, perchlorate, perbromate, periodate, antimonate, arsenate, nitrate, carbonate, the anion of a $C_1$–$C_8$ carboxylic acid, for example formate, acetate, propionate, butyrate, benzoate, phenylacetate, mono-, di- or trichloro- or -fluoroacetate, sulfonates, for example mesylate, ethanesulfonate, propanesulfonate, n-butanesulfonate, trifluoromethanesulfonate (triflate), unsubstituted or $C_1$–$C_4$alkyl-, $C_1$–$C_4$alkoxy- or halo-, especially fluoro-, chloro- or bromo-substituted benzenesulfonate, for example tosylate, p-ethoxybenzenesulfonate, pentafluorobenzenesulfonate or 2,4,6-triisopropylbenzenesulfonate.

Further anionic ligands are organic radicals which carry negative charges, examples being $C_1$–$C_{12}$ alcoholates, especially $C_1$–$C_4$alcoholates, $C_5$–$C_{12}$acetylides or $C_4$–$C_8$cycloalkenyl radicals, e.g. cyclopentadienyl.

Particularly preferred anionic ligands are H⁻, F⁻, Cl⁻, Br⁻, $BF_4^-$, $PF_6^-$, $SbF_6^-$, $AsF_6^-$, $CF_3SO_3^-$, $C_6H_5$—$SO_3^-$, 4-methyl-$C_6H_5$—$SO_3^-$, 3,5-dimethyl-$C_6H_5$—$SO_3^-$, 2,4,6-trimethyl-$C_6H_5$—$SO_3^-$ and 4-$CF_3$—$C_6H_5$—$SO_3^-$, and also cyclopentadienyl (Cp⁻). Cl⁻ is particularly preferred.

Examples of bis-anionic ligands are the bisanions of diols, diamines and hydroxy amines, such as catechol, N,N'-dimethyl-1,2-benzenediamine, 2-(methylamino)phenol, 3-(methylamino)-2-butanol and N,N'-bis(1,1-dimethylethyl)-1,2-ethanediamine.

Neutral ligands $L_1$, and $L_2$ are primarily tertiary phosphines having 3 to 40, especially 3 to 30 and, with particular preference, 3 to 18 carbon atoms. They are preferably of the formula:

$$PR^1R^2R^3 \qquad (II),$$

in which $R^1$, $R^2$ and $R^3$ independently of one another are $C_1$–$C_{20}$alkyl, $C_4$–$C_{12}$cycloalkyl, $C_2$–$C_{11}$heterocycloalkyl, $C_6$–$C_{16}$aryl, $C_2$–$C_{16}$heteroaryl or $C_7$–$C_{16}$aralkyl, which may be substituted by one or more substituents selected from the group consisting of $C_1$–$C_6$alkyl, $C_1$–$C_6$alkoxy, $C_1$–$C_6$haloalkyl, $C_6$–$C_{16}$aryl, —$NO_2$, —$SO_3^-$, ammonium and halogen; or the radicals $R^1$ and $R^2$ together are tetra- or pentamethylene which may be substituted by one or more substituents from the group consisting of $C_1$–$C_6$alkyl, $C_1$–$C_6$haloalkyl, —$NO_2$ and $C_1$–$C_6$alkoxy and may be fused to 1 or 2 bivalent 1,2-phenylene radicals, and $R^3$ is as defined above.

Examples of alkyl are methyl, ethyl and the isomers of propyl, butyl, pentyl, hexyl, heptyl, octyl, nonyl, decyl, undecyl and dodecyl. An example of aryl-substituted alkyl is benzyl. Examples of alkoxy are methoxy, ethoxy and the isomers of propoxy and butoxy.

Some examples of cycloalkyl are cyclobutyl, cycloheptyl or cyclooctyl and, in particular, cyclopentyl and cyclohexyl. Examples of substituted cycloalkyl are methyl-, dimethyl-, trimethyl-, methoxy-, dimethoxy-, trimethoxy-, trifluoromethyl-, bistrifluoromethyl- and tristrifluoromethyl-substituted cyclopentyl and cyclohexyl.

Examples of aryl are phenyl and naphthyl. Examples of aryloxy are phenoxy and naphthyloxy. Examples of substituted aryl are methyl-, dimethyl-, trimethyl-, methoxy-, dimethoxy-, trimethoxy-, trifluoromethyl-, bistrifluoromethyl- and tristrifluoromethyl-substituted phenyl. An example of aralkyl is benzyl. Examples of substituted aralkyl are methyl-,dimethyl-, trimethyl-, methoxy-, dimethoxy-, trimethoxy-, trifluoromethyl -, bistrifluoromethyl-and tristrifluoromethyl-substituted benzyl.

Heterocycloalkyl has preferably one or two heteroatoms and heteroaryl one to four heteroatoms, the heteroatoms being selected from the group consisting of oxygen, sulfur and nitrogen. Some examples of heterocycloalkyl are tetrahydrofuryl, pyrrolidinyl, piperazinyl and tetrahydrothienyl. Some examples of heteroaryl are furyl, thienyl, pyrrolyl, pyridyl and pyrimidinyl.

Preference is given to compounds (I), and their use, in which $L_1$ and $L_2$ independently of one another are tertiary phosphine of the formula II in which $R^1$, $R^2$ and $R^3$ are identical. Particular preference is given, furthermore, to radicals $R^1$, $R^2$ and $R^3$ which are sterically bulky, such as cyclic or branched alkyl groups, especially $\alpha,\alpha$-dibranched alkyl groups and, with particular preference, $\alpha$-branched alkyl groups.

Particular preference is given to compounds (I), and their use, in which $R^1$, $R^2$ and $R^3$ are methyl, ethyl, n- or i-propyl, n-, i-, s- or t-butyl, 1-, 2- or 3-pentyl, 1-, 2-, 3- or 4-hexyl, cyclopentyl, cyclohexyl, phenyl, naphthyl or benzyl, e.g. $(i\text{-}C_3H_7)_3P$, $(C_5H_9)_3P$ and $(C_6H_{11})_3P$.

In a compound (I) $R_a$ and $R_b$ independently of one another are hydrogen or hydrocarbon radicals. The term hydrocarbon radical embraces the definitions given above under compounds (II) for $R^1$, $R^2$ and $R^3$, especially the aliphatic, cycloaliphatic or cycloaliphatic-aliphatic substituents, carbocyclic aryl radicals or aryl-aliphatic radicals, and heterocycloalkyl and heteroaryl radicals with the said further substituents that are mentioned there.

In a compound (I) $R_a$ and $R_b$ independently of one another are $C_1$–$C_{20}$alkyl, $C_3$–$C_8$cycloalkyl, $C_3$–$C_7$heterocycloalkyl, $C_6$–$C_{14}$aryl or $C_4$–$C_{15}$heteroaryl, it being possible for these substituents to be substituted by one or more substituents from the group consisting of $C_1$–$C_4$alkyl, $C_1$–$C_4$-haloalkyl, $C_1$–$C_4$alkoxy, $C_6$–$C_{10}$aryl, $C_6$–$C_{10}$aryloxy, —$NO_2$ and halo.

In a particularly preferred embodiment $R_a$ and $R_b$ are $C_1$–$C_4$alkyl, especially methyl.

The invention additionally provides stereoisomeric compounds (I) which result from the presence of a centre of chirality in one of the said ligands or in a side chain. These instances of isomerism embrace optically pure enantiomers, diastereomers, and racemic mixtures.

The invention preferably relates to compositions comprising compounds of the formula

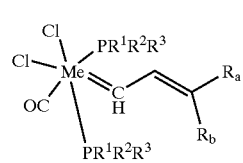

(I')

in which $R^1$, $R^2$ and $R^3$ independently of one another are $C_1$–$C_{20}$alkyl, $C_4$–$C_{12}$cycloalkyl, $C_2$–$C_{11}$heterocycloalkyl, $C_6$–$C_{16}$aryl, $C_2$–$C_{15}$heteroaryl or $C_7$–$C_{16}$aralkyl, which can be substituted by one or more substituents selected from the group consisting of $C_1$–$C_6$alkyl, $C_1$–$C_6$alkoxy, $C_1$–$C_6$haloalkyl, $C_6$–$C_{16}$aryl, —$NO_2$, —$SO_3^-$, ammonium and halogen, or the radicals $R^1$ and $R^2$ together are tetra- or pentamethylene, which can be substituted by one or more substituents from the group consisting of $C_1$–$C_6$alkyl, $C_1$–$C_6$haloalkyl, —$NO_2$ and $C_1$–$C_6$-alkoxy and can be fused to 1 or 2 bivalent 1,2-phenylene radicals, and $R^3$ is as defined above; and $R_a$ and $R_b$ independently of one another are $C_1$–$C_{20}$alkyl, $C_4$–$C_{12}$cycloalkyl, $C_2$–$C_{11}$heterocyclo-alkyl, $C_6$–$C_{16}$aryl, $C_2$–$C_{15}$heteroaryl or $C_7$–$C_{16}$aralkyl, which can be substituted by one or more substituents selected from the group consisting of $C_1$–$C_6$alkyl, $C_1$–$C_6$alkoxy, $C_1$–$C_6$haloalkyl, $C_6$–$C_{16}$aryl, —$NO_2$, $SO_3^-$, ammonium and halogen, and isomers of these compounds.

One particularly preferred embodiment relates to compositions in which in compounds (I') $R^1$, $R^2$ and $R^3$ are isopropyl, cyclopentyl or cyclohexyl and $R_a$ and $R_b$ are $C_1$–$C_4$alkyl.

The invention additionally provides compounds (I) in which

Me is ruthenium or osmium;

X and Y independently of one another are anionic ligands or together are a bis-anionic ligand;

$L_1$, and $L_2$ independently of one another are neutral ligands having electron donor properties, and $R_a$ and $R_b$ independently of one another are hydrogen or hydrocarbon radicals, and isomers of these compounds, with the exception of compounds (I) in which $L_1$ and $L_2$ are triisopropyl and one of the radicals $R_a$ and $R_b$ is hydrogen and the other is phenyl or both are phenyl.

One particularly preferred embodiment relates to compounds (I) in which $R^1$, $R^2$ and $R^3$ and also $R_a$ and $R_b$ are as defined, with the exception of compounds (I) in which $L_1$ and $L_2$ are triisopropyl and one of the radicals $R_a$ and $R_b$ is hydrogen and the other is phenyl or both radicals are phenyl.

One very particularly preferred embodiment relates to the compounds (I') in which $R^1$, $R^2$ and $R^3$ are isopropyl, cyclopentyl or cyclohexyl and $R_a$ and $R_b$ are $C_1$–$C_4$alkyl, especially methyl, and to their use.

The invention likewise relates to a process for preparing compounds (I) in which X, Y, $L_1$, $L_2$, $R_a$ and $R_b$ are as defined in claim 1, which comprises reacting a compound of the formula

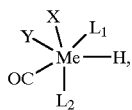

(III)

in which X, Y, L$_1$, and L$_2$ are as defined with a compound which introduces the group

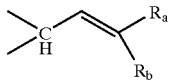

(IVa)

and isolating the desired compound (I) or (I').

In a compound (III) X, Y, L$_1$ and L$_2$ have the stated preferred definitions, for example X and Y are preferably chloro and L$_1$ and L$_2$ are preferably (i-C$_3$H$_7$)$_3$P, (C$_5$H$_9$)$_3$P or (C$_6$H$_{11}$)$_3$P.

A compound which introduces the group IV a is preferably a compound of the formula

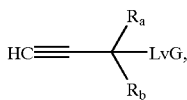

(IV)

in which R$_a$ and R$_b$ are as defined and LvG is a leaving group.

A leaving group LvG is preferably halo, for example chloro, bromo or iodo, or an organosulfonyl radical, e.g. mesyl, p-toluenesulfonyl or trifluoromethanesulfonate.

The process of the invention is advantageously conducted such that the compounds of the formula III are dissolved in a solvent and then the alkyne (IV) in question is added. The mass ratio of compounds of the formula III to compounds of the formula IV is generally in the range from 1:1 to 1:100, with preference being given to a ratio in the range from 1:1 to 1:5. The reaction takes place advantageously at temperatures of customary coolant mixtures to the boiling point of the solvent that is used, in particular at temperatures from about −50 to 150° C., preferably from −30 to 100° C. and, with particular preference, from −20 to −50° C.

Compounds of the formula III are known. Their preparation is described by M. A. Esteruelas et al. in *J. Organomet. Chem.* 303 (1986)221–231.

The cyclic olefins present in the compositions of the present invention can be monocyclic or polycyclic, fused and/or bridged ring systems, which have, for example, from two to four rings and which are unsubstituted or substituted and may contain heteroatoms such as O, S, N or Si in one or more rings and/or fused aromatic or heteroaromatic rings such as o-phenylene, o-naphthylene, o-pyridinylene or o-pyrimidinylene. The individual cyclic rings may contain 3 to 16, preferably 3 to 12 and, with particular preference, 3 to 8 ring members. The cyclic olefins may contain further nonaromatic double bonds depending on ring size, preferably from 2 to 4 such additional double bonds. The ring substituents involved are those which are inert; in other words, those which do not impair the chemical stability of the ruthenium and osmium compounds. The cycloolefins are strained rings or ring systems.

If the cyclic olefins contain more than one double bond, for example 2 to 4 double bonds, then depending on the reaction conditions, on the chosen monomer and on the amount of catalyst it is also possible for crosslinked polymers to be formed.

Fused-on alicyclic rings contain preferably 3 to 8, more preferably 4 to 7 and, with particular preference, 5 or 6 ring carbon atoms.

The cyclic olefins which are present in the composition and which can be polymerized with the aid of the catalysts of the invention are known and are described, for example, in WO 96/20235.

The composition of the invention may include inert solvents. A particular advantage in this case is that, with liquid monomers, a metathesis polymerization can be carried out without the use of a solvent. A further advantage is that the polymerization can even be carried out in water, polar and protic solvents, or water/solvent mixtures. In such cases it is of advantage, in the context of the present invention, to use a surfactant.

Examples of suitable inert solvents are protic polar and aprotic solvents, which can be used alone or in mixtures of at least two solvents. Examples are ethers (dibutyl ether, tetrahydrofuran, dioxane, ethylene glycol monomethyl or -dimethyl ether, ethylene glycol monoethyl or diethyl ether, diethylene glycol diethyl ether, triethylene glycol dimethyl ether), halogenated hydrocarbons, etc.

Compositions of the invention comprising a cycloolefin, for example dicyclopentadiene (DCPD), optionally with a cycloolefin and catalyst, are insensitive to oxygen and moisture, which permits storage and reaction without an inert gas.

In the context of the present invention, catalytic amounts denote preferably an amount from 0.001 to 20 mol%, with particular preference from 0.01 to 15 mol% and, with very particular preference, from 0.01 to 10 mol%, based on the amount of monomer. On the basis of the high thermocatalytic activity, very particular preference is given to amounts from 0.001 to 2 mol%.

The composition of the invention that is used for the polymerization can be prepared directly prior to polymerization or can be used in the form of a preformulated mixture, since the catalysts used are of particularly high stability. The mixture may even be stored for a prolonged period in the dark prior to polymerization, as a ready-to-use formulation, which is of advantage for large-scale industrial use.

The composition of the invention can comprise additives suitable for polymers, especially antioxidants, which are preferably used as formulating auxiliaries to improve the chemical and physical properties. The auxiliaries can be present in surprisingly high proportions without adversely affecting the polymerization; for example, in amounts of up to 70% by weight, preferably from 1 to 70% by weight, more preferably from 5 to 60% by weight and, with particular preference, from 10 to 50% by weight and, with special preference, from 10 to 40% by weight, based on the composition. Such auxiliaries have been disclosed in large numbers and are set out by way of example in the following list of auxiliaries:

1. Antioxidants 1.1. Alkylated monorhenols, for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(a-methylcyclohexyl)-4,6-dimethylphenol, 2,6-dioctadecyl-4-methylphenol, 2,4,6-tricyclohexylphenol, 2,6-di-tert-butyl-4-methoxymethylphenol, linear or sidechain-branched nonylphenols, such as 2,6-dinonyl-4-methylphenol, 2,4-dimethyl-6-(1'-methylundec-1'-yl) phenol, 2,4-dimethyl-6-(1'-methyl-heptadec-1'-yl)phenol, 2,4-dimethyl-6-(1l'-methyltridec-1'-yl)phenol and mixtures thereof.

1.2. Alkylthiomethylrphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecyl-thiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octa-decyloxyphenol, 2,6-di-tert-butylhydroquinone, 2,5-di-tert-butyl-4-hydroxyanisole, 3,5-di-tert -butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclo-hexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert -butylphenol), 2,2'-ethylidenebis(6-tert-butyl-4-isobutylphenol), 2,2'-methylenebis[6-(α-methyl-benzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1 ,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl] terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.7. O- N- and S-benzyl compounds, for example 3,5,3', 5'-tetra-tert-butyl-4,4'-dihydroxy-dibenzyl ether, octadecyl 4-hydroxy-3,5-dimethylbenzylmercaptoacetate, tridecyl 4hydroxy-3,5-di-tert-butylbenzylmercaptoacetate, tris(3,5-di-tert-butyl-4-hydroxybenzyl)-amine, bis(4-tert-butyl-3-hydroxy-2,6-dimethylbenzyl) dithioterephthalate, bis(3,5-di-tert-butyl-4-hydroxybenzyl) sulfide, isooctyl 3,5-di-tert-butyl-4-hydroxybenzylmercaptoacetate.

1.8. Hydroxybenzylated malonates, for example dioctadecyl 2,2-bis(3,5-di-tert-butyl-2-hydroxybenzyl)malonate, dioctadecyl 2-(3-tert-butyl-4-hydroxy-5-methylbenzyl) malonate, didodecyl mercaptoethyl-2,2-bis(3,5-di-tert-butyl-4-hydroxybenzyl)malonate, di-[4-(1 ,1,3,3-tetramethylbutyl)phenyl]2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxy-benzyl)-2,4,6-trimethylbenzene, 1,4-bis(3,5-di-tert-butyl-4-hydroxybenzyl)-2,3,5,6-tetra-methylbenzene, 2,4,6-tris(3,5-di-tert-butyl-4-hydroxybenzyl)phenol.

1.10. Triazine compounds, for example 2,4-bisoctylmercapto-6-(3,5-di-tert-butyl-4-hydroxy-anilino)-1, 3,5-triazine, 2-octylmercapto-4,6-bis(3,5-di-tert-butyl-4-hydroxyanilino)-1,3,5-triazine, 2-octylmercapto-4,6-bis(3, 5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1 ,3 ,5-triazine, 1 ,3,5-tris(3,5-di-tert-butyl-4-hydroxyphenylpropionyl)hexahydro-1,3,5-triazine, 1,3,5-tris(3,5-dicyclohexyl-4-hydroxybenzyl) isocyanurate.

1.11. Benzylphosphonates, for example dimethyl 2,5-di-tert-butyl-4-hydroxybenzyl-phosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzyl-phosphonate, the calcium salt of the monoethyl ester of 3,5-di-tert-butyl-4-hydroxybenzyl-phosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3.5-di-tert-butyl-4-hydroxyphenyl) prorionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxalamide, 3-thiaundecanol, 3-thiapentadecanol, trimethylhexanediol, trimethylolpropane, 4-hydroxymethyl-i-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxalamide, 3-thiaundecanol, 3-thiapentadecanol, trimethylhexanediol, trimethylolpropane, 4-hydroxymethyl-1-phospha-2,6,7-trioxa-bicyclo[2.2.2]octane.

1.15. Esters of β-(3.5-dicyclohexyl-4-hydroxyrhenyl) grogionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) -oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3.5-di-tert-butyl-4-hydroxyphenylacetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)-oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid, e.g. N,N'-bis(3,5-di-tert-butyl-4-hydroxyphenylpropionyl)hexamethylenediamide, N,N'-bis(3,5-di-tert-butyl-4-hydroxy -phenylpropionyl)trimethylenediamide, N,N'-bis(3,5-di-tert-butyl-4-hydroxyphenylpropionyl-hydrazide, N,N'-bis[2-(3-[3,5-di-tert-butyl-4-hydroxyphenyl]propionyloxy)ethyl]oxamide (Naugard® XL-1 from Uniroyal).

1.18. Ascorbic acid (vitamin C).

1.19. Aminic antioxidants, for example N,N'-diisopropyl-p-phenylenediamine, N,N'-di-sec-butyl-p-phenyienediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di-(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)N'-phenyl-p-phenylenediamine, N-cyclohexyl-N'-phenyl-p-phenylenediamine, 4-(p-toluenesulfonamido)-diphenylamine, N,N'-dimethyl-N,N'-di-sec-butyl-p-phenylenediamine, diphenylamine, N-aliyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyidiphenylamine, 4-n-butylaminophenol, 4-butyrylaminophenol, 4-nonanoylaminophenol, 4-dodecanoylaminophenol, 4-octadecanoylaminophenol, di-(4-methoxyphenyl)amine, 2,6-di-tert-butyl-4-dimethylaminomethylphenol, 2,4'-diamino-diphenylmethane, 4,4'-diaminodiphenylmethane, N,N,N',N'-tetramethyl-4,4'-diamino-diphenylmethane, 1,2-di[(2-methylphenyl)aminoethane, 1,2-di(phenylamino)propane, (o-tolyl)biguanide, di[4-(1',3'-dimethylbutyl)phenyl]amine, tert-octylated N-phenyl-1-naphthylamine, a mixture of mono- and dialkylated tert-butyl/tert-octyidiphenylamines, a mixture of mono- and dialkylated nonyidiphenylamines, a mixture of mono- and dialkylated dodecyidiphenylamines, a mixture of mono- and dialkylated isopropylasohexyl-diphenyl -amines, mixtures of mono- and dialkylated tert-butyldiphenylamines, 2,3-dihydro-3,3-dimethyl-4H-1,4-benzothiazine, phenothiazine, a mixture of mono- and dialkylated tert-butyl/tert-octyl-phenothiazines, a mixture of mono- and dialkylated tert-octyl-phenothiazines, N-allylphenothiazine, N,N,N',N'-tetraphenyl-1,4-diaminobut-2-ene, N,N-bis(2,2,6,6-tetra-methylpiperidin-4-yl)hexamethylenediamine, bis(2,2,6,6-tetramethylpiperidin-4-yl) sebacate, 2,2,6,6-tetramethylpiperidin-4-one and 2,2,6,6-tetramethylpiperidin-4-ol.

2. UV absorbers and light stabilizers 2.1. 2-(2'-Hydroxyhenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxy-phenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxy-phenyl-benzotriazole, 2-(2'-hydroxy-4'-octoxyphenyl)benzotriazole, 2-(3',5'di-tert-amyl-2'-hydroxy-phenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxyzcarbonylethyl]-2'-hydroxyphenyl)-5-chlorobenzotriazole 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethyl-hexyloxy)carbonylethyl]-2'-hydroxyphenyl)benzotriazole, 2-(3'-dodecyl-2'-hydroxy-5'-methyl-phenyl)benzotriazole, 2-(3'-tert-butyl-2'-hydroxy-5'-(2-isooctyloxycarbonylethyl) phenyl-benzotriazole, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxy-phenyl]benzotriazole with polyethylene glycol 300;

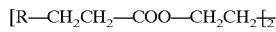

where R=3'-tert-butyl-4'-hydroxy-5'-2H-benzotriazol-2-yl-phenyl; 2-[2'-hydroxy-3'-(α,α-dimethylbenzyl)-5'-(1,1,3,3-tetramethylbutyl)phenyl-benzotriazole; 2-[2'-hydroxy-3'-(1,1,3,3-tetramethylbutyl)-5'-(α,α-dimethylbenzyl)phenyl]-benzotriazole.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of substituted or unsubstituted benzoic acids, for example 4-tert-butyl-phenyl salicylate, phenyl salicylate, octylphenyl salicylate, dibenzoylresorcinol, bis(4-tert-butyl-benzoyl)resorcinol, benzoylresorcinol, 2,4-di-tert-butylphenyl 3,5-di-tert-butyl-4-hydroxy-benzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate or isooctyl α-cyano-β,β-diphenylacrylate, methyl α-carbomethoxycinnamate, methyl α-cyano-β-methyl-p-methoxy-cinnamate or butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetra-methylbutyl)phenol], such as the 1:1 or 1:2 complex, with or without additional ligands such as n-butylamine, triethanolamine or N-cyclohexyldiethanolamine, nickel dibutyldithiocarbamate, nickel salts of monoalkyl esters, such as of the methyl or ethyl ester, of 4-hydroxy-3,5-di-tert-butylbenzylphosphonic acid, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidin-4-yl) sebacate, bis(2,2,6,6-tetramethylpiperidin-4-yl) succinate, bis(1,2,2,6,6-pentamethylpiperidin-4-yl)sebacate, bis(1-octyloxy-2,2,6,6-tetramethylpiperidin-4-yl) sebacate, bis(1,2,2,6,6-pentamethylpiperidyl) n-butyl-3,5-di-tert-butyl-4-hydroxybenzylmalonate, the condensate of 1-hydroxyethyl-2,2,6,6-tetramethyl-4-hydroxypiperidine and succinic acid, the linear or cyclic condensates of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, the linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro(4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, the condensate of N,N'-bis(2,2,6,6-tetramethyl-4-piperidyl)-hexamethylenediamine and 4-cyclohexylamino-2,6-dichloro-1,3,5-triazine, the condensate of 1,2-bis(3-aminopropylamino)ethane and 2,4,6-trichloro-1,3,5-triazine and also 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6-pentamethyl-4-piperidyl)-n-dodecyl-succinimide, 2-undecyl-7,7,9,9-tetramethyl-i-oxa-3,8-diaza-4-oxospiro[4.5]decane, the reaction product of 7,7,9,9-tetramethyl-2-cycloundecyl-1-oxa-3,8-diaza-4-oxo-spiro[4.5]decane and epichlorohydrine, 1,1-bis(1,2,2,6,6-pentamethyl-4-piperidyloxy -carbonyl)-2-(4-methoxyphenyl) ether, N,N'-bisformyl-N,N'-bis(2,2,6,6-tetramethyl-4-piperidyl) hexamethylenediamine, the diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, the reaction product of maleic anhydride-α-olefin copolymer and 2,2,6,6-tetramethyl-4-aminopiperidine or 1,2,2,6,6-pentamethyl-4-aminopiperidine.

2.7. Oxalamides, for example 4,4'-dioctyloxyoxanilide, 2,2'-diethoxyoxanilide, 2,2'dioctyloxy-5,5'-di-tert-butyloxanilide, 2,2'-didodecyloxy-5,5'-di-tert-butyloxanilide, 2-ethoxy-2'-ethytoxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy- and of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis -(2,4-dimethylphenyl)-1,3,5-triazine, 2-(2-hydroxy-4-tridecyloxyphenyl)-4,6-bis-(2,4-dimethylphenyl)-1,3,5-triazine, 2-[2-hydroxy-4-(2-hydroxy-3-butyloxypropybxy) phenyl]-4,6-bis(2,4-dimethylphenyl)-1,3,5-triazine, 2-[2-hydroxy-4-(2-hydroxy-3-octyloxypropyloxy)-phenyl]-4,6-bis(2,4-dimethylphenyl)-1,3,5-triazine, 2-[4-(dodecyloxy/tridecyloxy-2-hydroxypropoxy)-2-hydroxyphenyl]-4,6-bis (2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5triazine, 2-{2-hydroxy-4-]3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxalamide, N-salicylal-N'-salicyloyl hydrazine, N,N'-bis(salicyloyl)hydrazine, N,N'-bis(3,5-di-tert-butyl-4-hydroxyphenyl-propionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites, phosphines and phosphonites, for example triphenyl phosphite, diphenyl alkyl phosphites, phenyl dialkyl phosphites, tris(nonylphenyl)phosphite, trilauryl phosphite, trioctadecyl phosphite, trimethylphosphine, tri-n-butylphosphine, triphenylphosphine, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)pentaerythritol diphosphite, bisisodecyloxypentaerythritol diphosphite, bis(2,4-di-tert-butyl-6-methylphenyl)pentaerythritol diphosphite, bis(2,4,6-tri-tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-1 2H-dibenzo[d,g]-1 ,3,2-dioxaphosphocin, 6-fluoro-2,4,8,1 0-tetra-tert-butyl-1 2-methyl-dibenzo[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyl-tris(3,3',5,5'-tetra-tert-butyl-1,1'-biphenyl-2,2'-diyl)phosphite], 2-ethylhexyl (3,3',5,5'-tetra-tert-butyl-1,1'-biphenyl-2,2'-diyl)phosphite.

Particular preference is given to using the following phosphites: Tris(2,4-di-tert-butylphenyl)phosphite (Irgafos®68, Ciba-Geigy), tris(nonylphenyl)phosphite,

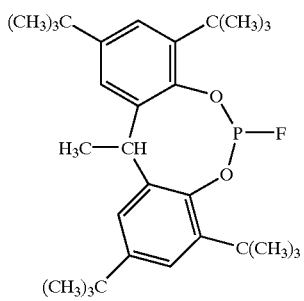 (A)

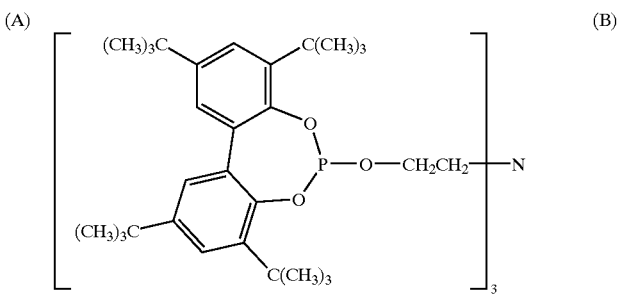 (B)

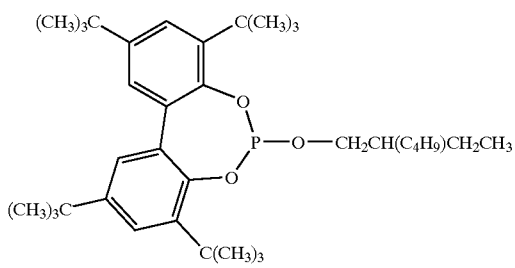 (C)

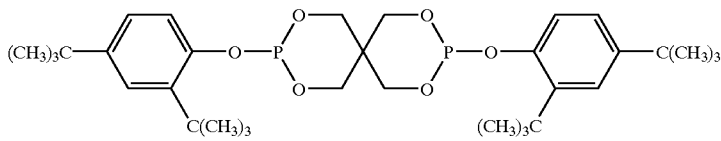 (D)

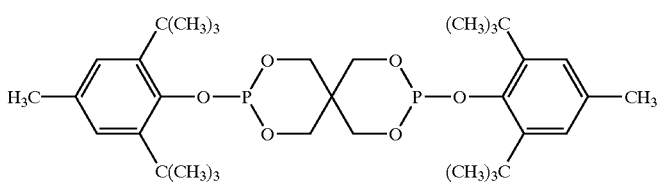 (E)

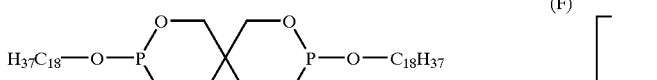 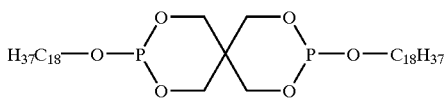 (F)

 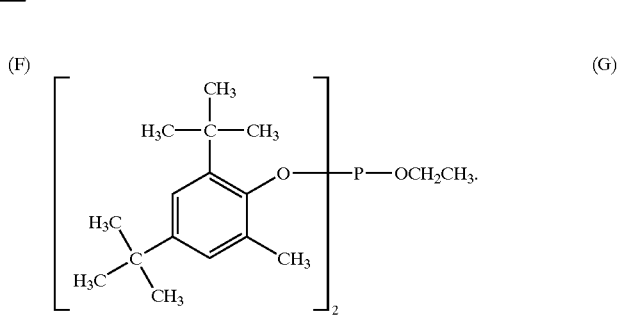 (G)

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine from hydrogenated tallow fatty amines.

6. Nitrones, for example N-benzyl alpha-phenyl nitrone, N-ethyl alpha-methyl nitrone, N-octyl alpha-heptyl nitrone, N-lauryl alpha-undecyl nitrone, N-tetradecyl alpha-tridecyl nitrone, N-hexadecyl alpha-pentadecyl nitrone, N-octadecyl alpha-heptadecyl nitrone, N-hexadecyl alpha-heptadecyl nitrone, N-octadecyl alpha-pentadecyl nitrone, N-heptadecyl alpha-heptadecyl nitrone, N-octadecyl alpha-hexadecyl-nitrone, and nitrones derived from N,N-dialkylhydroxylamines prepared from hydrogenated tallow fatty amines.

7. Thiosynergists, for example dilauryl thiodipropionate or distearyl thiodipropionate.

8. Peroxide scavengers, for example esters of 0-thiodipropionic acid, for example the lauryl, stearyl, myristyl or tridecyl esters, mercaptobenzimidazole, the zinc salt of 2-mercapto-benzimidazole, zinc dibutyidithiocarbamate, dioctadecyl disulfide, pentaerythritol tetrakis(β-dodecylmercapto)propionate.

9. Polvamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate, potassium palmitate, antimony pyrocatecholate or zinc pyrocatecholate.

11. Nucleating agents, for example inorganic substances, such as talc, metal oxides such as titanium dioxide or magnesium oxide, phosphates, carbonates or sulfates of, preferably, alkaline earth metals; organic compounds such as mono- or polycarboxylic acids and their salts, such as 4-tert-butylbenzoic acid, adipic acid, diphenyl acetic acid, sodium succinate or sodium benzoate; and polymeric compounds, for example ionic copolymers (ionomers).

12. Fillers and reinforcing agents, for example calcium carbonate, silicates, glass fibres, glass beads, talc, kaolin, mica, barium sulfate, metal oxides and hydroxides, carbon black, graphite, wood flour and flours or fibres of other natural products, and synthetic fibres.

13. Other additives, for example plasticizers, lubricants, emulsifiers, pigments, rheological additives, catalysts, levelling assistants, optical brighteners, flameproofing agents, antistatic agents, blowing agents.

14. Benzofuranones and indolinones, as described, for example, in U.S. Pat. No. 4,325,863; 4,338,244; 5,175,312, 5,216,052; 5,252,643; DE-A-4316611; DE-A-4316622; DE-A-4316876; EP-A-0589839 or EP-A-0591102, or 3-[4-(2-acetoxy-ethoxy)phenyl]-5,7-di-tert-butylbenzofuran-2-one, 5,7-di-tert-butyl-3-[4-(2-stearoyloxy-ethoxy)phenyl]benzofuran-2-one, 3,3'-bis[5,7-di-tert-butyl-3(4-[2-hydroxyethoxy]phenyly)-benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one.

The invention provides, furthermore, a process for preparing metathesis polymers, which comprises exposing
 (α) a cycloolefin, or mixture of cycloolefins and
 (β) a catalytic amount of at least one compound of the formula (I) as defined above, alone or in a mixture with further additives, to light and, if desired, subjecting the obtainable methathesis polymer to a shaping process.

The process of the invention is preferably carried out at a temperature of at least 0° C. In particular, the process of the invention is conducted at temperatures from 0° to 300° C., preferably from room temperature to 250° C., more preferably from room temperature to 200° C. and, with particular preference, from room temperature to 160° C. The radiation source used is UV or visible light. The process is conducted under the reaction conditions known for photoinduced polymerizations. Following the polymerization it may be advantageous to condition the polymers at elevated temperatures, for example from 80 to 200° C.

Polymerization can be combined with shaping processes such as calendering, casting, compression moulding, injection moulding or extrusion. With the process of the invention it is possible to produce materials for the machining production of shaped articles or thermo-plastically deformable materials for producing shaped articles of all kinds, and coatings. Advantageously, shaping and polymerization are combined in solvent-free reactive systems, it being possible to employ processing techniques such as injection moulding, extrusion, polymerization in predetermined forms (possibly under superatmospheric pressure).

The invention also provides the polymers obtainable by the process of the invention.

The polymers prepared by the process of the invention can be homopolymers or copolymers with random distribution of the structural units, graft polymers or block polymers, and also crosslinked polymers of this kind. They may have an average molecular weight ($\overline{Mw}$) of, for example, from 500 to 2 million daltons, preferably from 1000 to 1 million daltons (determined by GPC by comparison with polystyrene standards of narrow distribution).

The uncrosslinked or linear polymers comprise oligomers and polymers and can contain, for example, from 5 to 5000, advantageously from 10 to 2000, preferably from 20 to 1000, more preferably from 20 to 500 and, with particular preference, from 20 to 300 structural units. Where the polymers are processed further, preference is given to relatively low molecular weights, and in the case of processing to mouldings use is judiciously made of polymers having relatively high molecular weights.

Depending on the nature and amount of the monomers used, the polymers of the invention may have different properties. Some are notable for very high oxygen permeability, excellent dielectric properties (low dielectric constants, low loss factors or tan δ values), good thermal stability (glass transition temperatures above 100° C.), good toughnesses (impact and notched impact strength), flexibility and mechanical strengths (fracture resistance), hardness and a low degree of water absorption. Others have outstanding optical properties, such as high transparency and low refractive indices. Also deserving of particular emphasis are the low shrinkage and the excellent surface properties (smoothness, gloss, adhesion). They can therefore be used in a very wide variety of industrial fields.

As coats on the surfaces of substrate materials, the polymers of the invention are notable for high adhesive strength. In addition, the coated materials feature high surface smoothness and gloss. Among the good mechanical properties particular emphasis should be placed on the low shrinkage and high impact strength, and also the thermal stability. Also deserving of mention are the ease of demoulding and the high solvent resistance. The surfaces can be modified further, for example painted or printed, and the high adhesive strengths of the coatings should be mentioned in this case, too.

The polymers obtainable in accordance with the invention are particularly suitable for producing consumer articles of all kinds, such as mouldings for cars, boats, leisure articles, pallets, pipes, sheets, etc.; as insulating materials for producing electrical and electronic components; as implants; as binders for coating materials; as heat-curable compositions for modelling, or as adhesives for bonding substrates having low surface energies (Teflon, polyethylene or polypropylene). The compositions of the invention can also be used to prepare coatings, it being possible to use both clear (transparent) and even pigmented compositions. Both white pigments and colour pigments can be used. Mention should also be made of the production of shaped articles by thermoplastic shaping processes for consumer articles of all kinds.

The compositions of the invention are also suitable in particular for producing protective coats. The invention also provides a variant of the process of the invention for producing coated materials, in which the composition of the invention is applied with or without solvent as a film to a substrate, for example by dipping, brushing, flow coating, rolling, knife coating or spin coating techniques, the solvent (if used) is removed, and the film is heated for polymerization. With this process it is possible to modify or protect the surfaces of substrates (corrosion protection).

The present invention provides, furthermore, a coated substrate material wherein a coat of the polymer of the invention has been applied to a substrate.

The present invention likewise provides a coated substrate having a cured film of the polymer of the invention.

Examples of suitable substrates (carrier materials) are those of glass, minerals, ceramics, plastics, wood, semi-metals, metals, metal oxides and metal nitrides. The film thicknesses depend essentially on the desired use and can, for example, be from 0.1 to 1000 μm, preferably from 0.5 to 500 μm and, with particular preference, from 1 to 100 μm. The coated materials are notable for high adhesive strength and good thermal and mechanical properties.

The coated materials of the invention can be prepared by known methods such as brushing, knife coating and flow coating methods such as curtain coating or spin coating.

In the case of coatings, particularly good results are often achieved if the photoinduced metathesis polymerization is carried out with the additional use of cycloolefins which in addition contain 1 to three, and preferably one, further double bond and which in the context of the invention are polycyclic fused ring systems.

The examples which follow illustrate the invention.

EXAMPLE 1

Preparation of

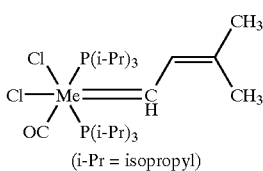

(i-Pr = isopropyl)

485 mg of Cl(CO)H(i-Pr$_3$P)$_2$Ru (prepared in analogy to the method described by M. A. Esteruelas etal. in *J. Organomet. Chem.* 303 (1986)221–231) are dissolved in 15 ml of methylene chloride and the solution is cooled to −60° C. 115 μl of 3-chloro-3-methyl-1-butyne in 10 ml of methylene chloride are added dropwise to the yellow suspension. This suspension is then left to warm slowly to room temperature, during which an orange-coloured solution is formed. The mixture is concentrated under reduced pressure and the orange-coloured solid residue obtainable is washed with three times five ml of hexane. The product is subsequently dried under reduced pressure to give 520 mg (88%) of an orange-coloured, yellowish powder. $^1$H-NMR (CDCl$_3$): δ=16.95 [d, 1, J=14.0 Hz,=CH—CH(CH$_3$)$_2$]; 7.95[d,1, J=13.9 Hz, =CH—CH(CH$_3$)$_2$]; 2.75 {m,6, P[CH(CH$_3$)$_2$]$_3$}; 1.76 [m,3,=CH—CH(CH$_3$)$_2$: 1.38–1.14{m, 39, =CH—CH(CH$_3$)$_2$+P[CH(CH$_3$)$_2$]$_3$};$^{31}$P-NMR (CDCl$_3$): δ=39.0. Elemental analysis [in %, calculated values in brackets]: C49.98(49.0)H8.68(8.56Cl12.10(12.05),P10.41 (10.52)

EXAMPLE 2

Preparation of

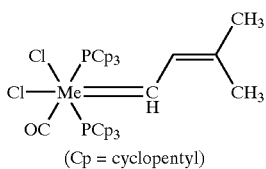

(Cp = cyclopentyl)

Reacting 500 mg of Cl(CO)H(PCp$_3$)$_2$Ru (prepared in analogy to the method described by M. A. Esteruelas et.al. in *J. Organomet. Chem.* 303(1986)221–231) with 90 ml of 3-chloro-3-methyl-1-butyne gives 495 mg of title compound (yield: 85%).

$^1$H-NMR (CDCl$_3$): δ=16.82 [d, 1, J=14.0 Hz,=CH—CH(CH$_3$)$_2$]; 7.88 [d, 1, J=13.8 Hz =CH—CH(CH$_3$)$_2$]; 2.76 {m,6, P[CH(CH$_2$)$_4$]$_3$}; 2.30–1.50 {m, 54,=CH—CH(CH$_3$)$_2$+P[CH(CH$_2$)$_4$]$_3$};$^{31}$P-NMR (CDCl$_3$): δ=28.6. Elemental analysis [in %, calculated values in brackets]: C,58.42 (58.05): H,8.42 (8.39): Cl,9.48 (9.52): P: 8.08 (8.32).

EXAMPLE 3

Preparation of

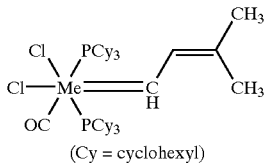

(Cy = cyclohexyl)

Reacting 500 mg of Cl(CO)H(PCy$_3$)$_2$Ru (prepared in analogy to the method described by M. A. Esteruelas et aL in *J. Organomet. Chem.* 303 (1986) 221–231) with 80 ml of 3-chloro-3-methyl-1-butyne gives 510 mg of the title compound (yield: 89%). $^1$H-NMR (CDCl$_3$): δ=16.93 [d, 1, J=14.0 Hz, =CH—CH(CH$_3$)$_2$]; 7.95 [d, 1J=13.9 Hz, =CH—CH(CH$_3$)$_2$]; 2.40–1.20 [m, 72,=CH—CH(CH$_3$)$_2$+PCy$_3$]$^{31}$P-NMR (CDCl$_3$): δ=29.4. Elemental analysis [in %, calculated values in brackets]: C, 60.71 (60.55): H, 9.08 (9.00): Cl, 8.48 (8.55): P: 7.30 (7.47).

EXAMPLE 4 (Use Examples)

The table below summarizes the results of polymerization reactions using the catalyst of Example 1. Exposure was carried out with a medium-pressure Hg lamp (Hönle: 80 mW/cm$^2$) to give a filmlike, flexible polymer.

| Monomer | | % by wt. of cat. | Exp. time (RT) | Latency (RT) | $T_g^1$ |
|---|---|---|---|---|---|
| NFJH 13 | 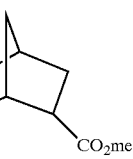 | 2.5 | 3 minutes | >2 months | 55° C. |

-continued

| Monomer | | % by wt. of cat. | Exp. time (RT) | Latency (RT) | $T_g{}^1$ |
|---|---|---|---|---|---|
| NFJH/cyclo hexenyl-NBE (1/1) | 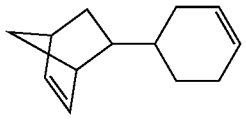 | 2.5 | 3 minutes | >2 months | |

$^1T_g$ after curing for 0.5–1 hour at 120° C.

EXAMPLE 5 (Use Examples)

The table below summarizes the results of polymerization reactions using the catalyst of Example 1. Exposure was carried out with a medium-pressure Hg lamp (Hönle: 80 mW/cm$^2$) to give a filmlike, flexible polymer.

| Monomer | % by wt. of cat. | Exp. time (RT) | Latency (RT) | $T_g{}^1$ |
|---|---|---|---|---|
| 1 | 2.5 | 3 minutes | >2 months | 55° C. |
| 1 | 1.0 | 15 minutes | >2 months | 52° C. |
| 1 | 0.5 | 15 minutes | >2 months | 50° C. |
| 1 and 2 (1:1) | 2.5 | 3 minutes | >2 months | 65° C. |
| 3 | 0.7 | 10 minutes | >1 month | 60° C. |
| 4 | 1.0 | 5 minutes | >1 month | 90° C. |

$^1T_g$ after curing for 0.5–1 hour at 120° C.

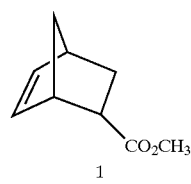

1

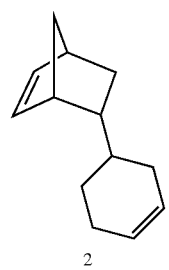

2

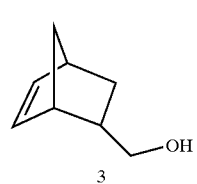

3

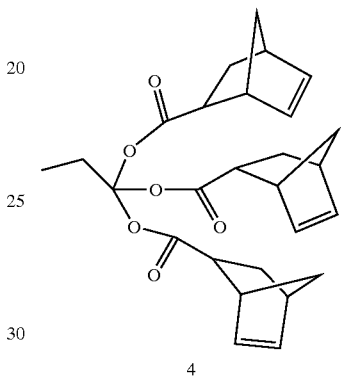

4

What is claimed is:

1. A composition comprising
   (a) a cycloolefin or a mixture of cycloolefins; and
   (b) a catalytic amount of at least one compound of the formula (I')

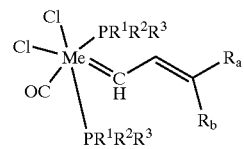

(I')

in which
Me is ruthenium or osmium and
R$^1$, R$^2$ and R$^3$ are isopropyl, cyclopentyl or cyclohexyl and R$_a$ and R$_b$ are C$_1$–C$_4$-alkyl,
and isomers of these compounds.

2. A composition according to claim 1 which additionally comprises an antioxidant.

3. A compound of the formula (I')

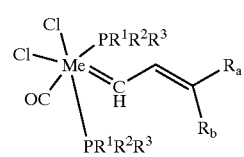

(I')

in which
Me is ruthenium or osmium and
R$^1$, R$^2$ and R$^3$ are isopropyl, cyclopentyl or cyclohexyl and R$_a$ and R$_b$ are C$_1$–C$_4$-alkyl, 4. A compound of the formula (I') according to claim 3 in which $R^1$, $R^2$ and $R^3$ are isopropyl.

5. A process for preparing a compound of formula (I') according to claim 3, which comprises reacting a compound of the formula (III')

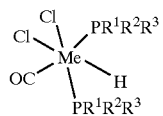
(III')

with a compound which introduces the group (IVa)

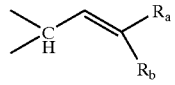
(IVa)

and isolating the desired compound, wherein $R^1$, $R^2$, $R^3$, $R_a$ and $R_b$ are as defined in claim 3.

6. A process according to claim 5, wherein the compound which introduces the group (IVa) is a compound of the formula

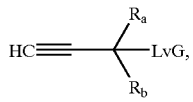
(IV)

in which $R_a$ and $R_b$ are as defined and LvG is a leaving group.

7. A process for preparing a metathesis polymer, which comprises exposing a composition comprising
(a') a cycloolefin, or mixture of cycloolefins and
(b') a catalytic amount of at least one compound of the formula (I')

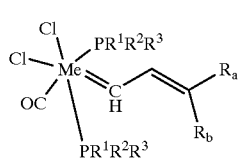
(I')

in which
Me is ruthenium or osmium and
$R^1$, $R^2$ and $R^3$ are isopropyl, cyclopentyl or cyclohexyl and $R_a$ and $R_b$ are $C_1$–$C_4$-alkyl,
and isomers of these compounds alone or in a mixture with further additives, to light and, optionally, subjecting the obtained metathesis polymer to a shaping process.

* * * * *